(12) United States Patent
Kimura et al.

(10) Patent No.: US 6,396,065 B1
(45) Date of Patent: May 28, 2002

(54) RADIOACTIVE RAY IRRADIATING APPARATUS

(75) Inventors: Masakazu Kimura; Takeshi Hirano, both of Tokyo (JP)

(73) Assignee: Mitsubishi Denki Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/395,225

(22) Filed: Sep. 14, 1999

(30) Foreign Application Priority Data

Dec. 1, 1998 (JP) .......................................... 10-342044

(51) Int. Cl.$^7$ ............................. G01N 21/00; G21G 5/00
(52) U.S. Cl. ............................. 250/453.11; 250/455.11; 250/492.3
(58) Field of Search ....................... 250/453.11, 454.11, 250/492.3, 455.11

(56) References Cited

U.S. PATENT DOCUMENTS

| | | | | |
|---|---|---|---|---|
| 4,849,641 A | * | 7/1989 | Berkowitz ................ | 250/492.3 |
| 5,004,926 A | * | 4/1991 | Vassenaix et al. ........ | 250/492.3 |
| 5,321,271 A | * | 6/1994 | Schonberg et al. ....... | 250/492.3 |
| 5,396,074 A | * | 3/1995 | Peck et al. .............. | 250/454.11 |
| 5,635,714 A | * | 6/1997 | Nablo et al. ............. | 250/492.3 |
| 6,215,847 B1 | * | 4/2001 | Perrins et al. .......... | 250/453.11 |

FOREIGN PATENT DOCUMENTS

| | | |
|---|---|---|
| JP | 9043164 | 2/1997 |
| JP | 1101897 | 4/1999 |

* cited by examiner

*Primary Examiner*—Bruce Anderson
(74) *Attorney, Agent, or Firm*—Rothwell, Figg, Ernst & Manbeck (57) ABSTRACT

In projecting radioactive rays for sanitizing food or the like, an irradiating condition which attains a uniform dose of radioactive rays for the entire objects to be exposed is automatically determined. An X-ray CT unit 6 captures a sectional image of an object to be exposed 2, and an irradiating condition determining section 8 acquires the density distribution of the object to be exposed 2 based on the captured sectional image. The irradiating condition determining section 8 then searches for a particular irradiating condition under which the dose distribution of the radioactive rays in the object to be exposed 2 falls within a predetermined range. An irradiation controlling section 16 controls a radioactive ray irradiating unit 14 based on the irradiating condition, and projects radioactive rays to the object to be exposed 2 in accordance with the irradiation condition when the object is transported to the radioactive ray irradiating unit 14 by a belt conveyor.

12 Claims, 5 Drawing Sheets

RADIOACTIVE RAY IRRADIATING APPARATUS

BACKGROUND OF THE INVENTION

1. Field of the Invention

The present invention generally relates to a radioactive ray irradiating apparatus, and more particularly to a radioactive ray irradiating apparatus which can reliably carry out sterilization, pasteurization, termination of pests, and/or inhibition of germination by projecting radioactive rays.

2. Description of the Related Art

Radioactive ray irradiating apparatuses have been known for irradiating medical instruments, such as artificial dialyzers, syringe needles, surgical gloves, or medical containers, with radioactive rays for sterilizing such instruments prior to usage. Such apparatuses emit radioactive rays to a case in which medical instruments are stored. Since the density of the contents of the case is not uniform, it is difficult to determine the dose of radioactive rays at points in the case only by calculation. Therefore, it is necessary to irradiate the case with radioactive rays in advance to measure the actual dose of radioactive rays at points in the case, thereby determining a particular irradiating condition under which sterilization can be carried out reliably regardless of the arrangement of medical instruments stored in the case.

Specifically, this is done by providing a plurality of small radioactive ray sensors, such as film dosemeters sensitive to radioactive rays, at several points in the case together with the medical instruments, and then projecting the radioactive rays so that the sensors measure the actual dose values to determine appropriate irradiating conditions.

Radioactive rays are also used for treating diseases such as malignant tumors. In the treatment, lesions of malignant tumors or the like are irradiated with radioactive rays so that the tumor cells absorb the radiation energy and disappear. An apparatus called an X-ray CT (computed tomography) or images captured by this apparatus are used in the treatment for determining the irradiation field and conditions of radioactive rays. Specifically, the X-ray CT apparatus captures a sectional image of a patient and locates the tumor lesions, whereby the irradiation field and conditions are determined in a manner maximizing the amount of radioactive energy absorption of the tumor lesions and minimizing that of normal tissues.

Studies have been made in other industrial fields to use radioactive ray effects, especially the effect of imparting the energy of radioactive rays to cells. For instance, the FAO (Food and Agriculture Organization of the United Nations) and the CAC (the Secretariat of the Codex Alimentarius Commission) of the WHO (World Health Organization) have applied the irradiation of foods to other purposes, such as sterilization of putrefying bacteria or disease bacteria, termination of pests and parasites, germination control, or extension of food storage, and defined the standard dose for each application. Here, it is intended to realize the safe storage of food to thereby seek to find a solution to the food problem that is one of the most important issues of the world at moment.

Recently, the total abolition of using methyl bromide, which has been used for the termination of pests and parasites in the process of plant quarantine in Japan and many other countries, is under way. Since methyl bromide is an ozone layer destroying substance, it is a global trend to abolish the use and production of it, and the radioactive ray irradiation is considered as a promising candidate method for replacing methyl bromide. Examples of products imported to Japan to which plant quarantine is required are cut flowers, spices, crude drugs, fruits, grains, lumber, and many other types of products.

The conventional method described above for sterilizing medical instruments or the like that requires a preliminary procedure of determining the irradiating conditions using the radioactive ray sensors takes a lot of time due to repeated trial and error needed to find appropriate irradiating conditions. In particular, if the radioactive ray sensors formed by films or the like which cannot indicate measurement values real time are used, it may take quite a long time to determine the conditions. Such a problem may be allowed as long as the types of objects to be exposed are limited and the irradiation is repeated under the same conditions once the conditions are determined, as in the conventional irradiating method for medical instruments. However, when many kinds of objects to be exposed are provided and packed in a variety of styles, the complex condition determining procedure of the conventional method cannot be ignored.

In general, it is possible to project the radioactive rays having a sufficient strength necessary for sterilization to the objects to be exposed in the conventional irradiating method of medical instruments, because the objects to be exposed are not activated regardless of whether X-rays or gamma rays are used. Thus, what is important in determining the irradiating conditions is whether or not the sterilization is carried out sufficiently at a point indicating the minimum dose in the case, and it is not essentially a problem if there are some points indicating a particularly strong dose in the case. The uniform dose distribution is, therefore, not strictly required. However, if the objects to be exposed are food products or plants, radioactive rays will affect the objects themselves as well as the bacteria and pests to be sterilized which cling to the objects to be exposed. As a result of the excessive exposure to radioactive rays, taste, color, or smell, for example, of these objects may be changed by chemical reaction, causing unwanted events such as deterioration of food safety, lower nutrition of food, or flower death. Therefore, the irradiating conditions for these objects must be determined in such a manner that the objects are only made to suffer a limited amount of damage within an allowable range and that the purpose of irradiation such as sterilization can be carried out sufficiently. Generally, since there are not so many candidate conditions that meet the above requirements, the dose distribution has to be uniform in the irradiation area. Because of such additional requirements, it is more difficult to use the above trial-and-error type method to find irradiating conditions.

Meanwhile, the above-mentioned conventional radiotherapy system utilizes sectional images captured by the X-ray CT apparatus to identify a target irradiating area, and focuses the radioactive rays on the identified target area to determine the irradiating field and conditions so as to avoid irradiation of normal tissues as much as possible. Therefore, it is not possible to adopt this method without any modification for determining the irradiating conditions in the case that calls for the uniform dose distribution over the entire irradiating field.

SUMMARY OF THE INVENTION

The present invention is made to solve the above problems and aims to provide a radioactive ray irradiating apparatus capable of automatically determining irradiating conditions under which a uniform dose distribution is realized for the entire object to-be exposed, thereby saving time and cost taken for determining the irradiating conditions.

According to the present invention, a radioactive ray irradiating apparatus includes a tomographic image capturing means for imaging a sectional view of an object to be exposed along a direction of projecting radioactive rays to obtain a density distribution of the object to be exposed, and an irradiating condition determining means for determining irradiating conditions based on the density distribution of the object to be exposed so that the variation of the dose distribution of projected radioactive rays in the object to be exposed falls within a predetermined reference range. The apparatus projects the radioactive rays by controlling a radioactive ray irradiating means in accordance with the determined irradiating conditions.

In the radioactive ray irradiating apparatus according to the present invention, types of radioactive rays that can be projected from the radioactive ray irradiating means are electron beams and/or X-rays, and the irradiating condition determining means determines the irradiating conditions including the types of radioactive rays.

The radioactive ray irradiating apparatus according to the present invention further includes a transportation means for moving the object to be irradiated from the tomographic image capturing means to the radioactive ray irradiating means in such a manner that the object to be exposed passes through the radioactive ray irradiating means at a speed corresponding to a necessary irradiation dose and a radioactive ray output of the radioactive ray irradiating means.

DESCRIPTION OF PREFERRED EMBODIMENTS

Embodiments of the present invention will be described below with reference to the attached drawings.

[Embodiment 1]

Figure 1:
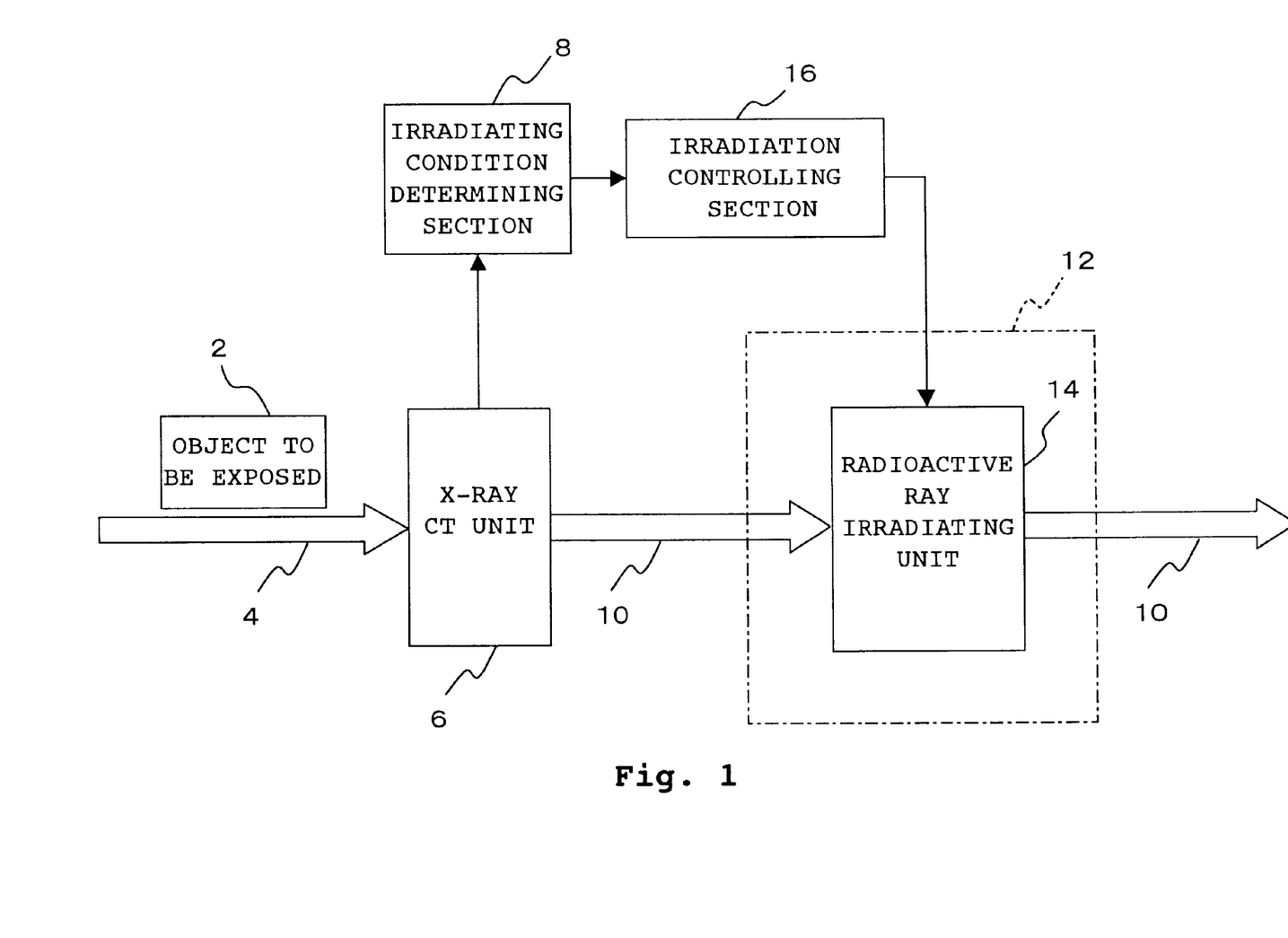
FIG. 1 is a schematic block diagram of a radioactive ray irradiating apparatus for plant quarantine according to a first embodiment of the present invention.

FIG. 1 is a schematic block diagram showing a radioactive ray irradiating apparatus used for plant quarantine according to one embodiment of the present invention. An object to be exposed 2 may be imported cut flowers, spices, crude drugs, fruits, grain, lumber, or the like which are often packaged in boxes. Shapes of the box (e.g., height, width, and depth) as well as materials and thickness thereof are different depending on the items to be stored. Some items may be packed in smaller lots before being put in a box. The object to be exposed 2 is one of these imported products brought to the apparatus of the present invention as a result of the sampling test conducted by quarantine officers who have judged that the treatment such as termination of pests is necessary for the object.

The object to be exposed 2 is put on a belt conveyor 4 and brought into a center hole of a scanner mechanism section (gantry) of a tomographic image capturing means formed by an X-ray CT unit 6. The X-ray CT unit 6 scans the object to be exposed 2 from multiple directions with fine X-ray beams and reproduces the tomographic image of the object 2 based on the penetration data. The tomographic image is the data consisting of CT values obtained at points of a section of the object 2 exposed to X-rays. Each CT value corresponds to the density at each point of the exposed section of the object 2 and the tomographic image corresponds to the density distribution of the section. The tomographic image is captured by shooting the object to be exposed 2 at several points while it is moved so as to pass through the center hole of the gantry from the inlet side to the outlet side. Thus, the information of three-dimensional density distribution of the object to be exposed 2 is obtained.

The tomographic data is transferred to an irradiating condition determining section 8 (an irradiating condition determining means) after being captured by the X-ray CT unit 6. Meanwhile, the object to be exposed 2 is put on a belt conveyor 10 and moved to pass through a radioactive ray irradiating unit 14 located in a shield room 12 surrounded by radioactive ray protecting walls.

The irradiating condition determining section 8 determines particular irradiating conditions using the tomographic image data, and an irradiation controlling section 16 controls the radioactive ray irradiating unit 14 based on the determined irradiating conditions. The radioactive ray irradiating unit 14 is a radioactive ray irradiating means which irradiates the object 2 with radioactive rays while the object 2 is put on the belt conveyor 10 and passes through the radioactive ray irradiating unit 14, thereby carrying out such treatment as termination of pests.

The radioactive ray irradiating unit 14 of the present apparatus includes a plurality of radioactive ray irradiating heads which can emit either X-rays or electronic beams, with each head facing the belt conveyor 10 from a different direction. For instance, in the case of two heads, they are arranged opposite to each other with respect to the belt conveyor 10. If three heads are provided, the heads are shifted from each other by 120 degrees about the belt conveyor 10, and if four heads are provided, pairs of two heads are arranged at opposite ends of one of two axes extending perpendicular to the belt conveyor 10. The energy of the radioactive rays emitting from each head can be changed independently. This arrangement can be realized with a plurality of accelerators, such as linear accelerators of the conventional art which have been used for high energy radiotherapy.

The radioactive ray irradiating unit 14 of the present apparatus has three controllable irradiating conditions, i.e., radioactive ray energy E, irradiating direction θ, and irradiation dose R. Since the irradiation dose R is determined as a product of the radioactive ray output I and the irradiation time t of the radioactive ray irradiating unit 14, it is possible to control R by controlling I or t. To control the irradiation time t, the output time of radioactive rays from the radioactive ray irradiating unit 14 may be adjusted, or the moving speed of the belt conveyor 10 may be adjusted to change time when the conveyor 10 passes the radioactive ray emitting point.

Having been irradiated by the radioactive ray irradiating unit 14, the object 2 on the belt conveyor 10 is taken out of the unit 14 and then from the shield room 12.

One feature of the present apparatus is that, based on the information of density distribution of the object to be exposed 2 indicated in the tomographic image data, the irradiating condition determining section 8 searches for appropriate irradiating conditions so that the variation of the dose distribution of the radioactive rays in the object 2 projected from the radioactive ray irradiating unit 14 falls below a predetermined reference value. This will be described in detail below.

Figure 2:
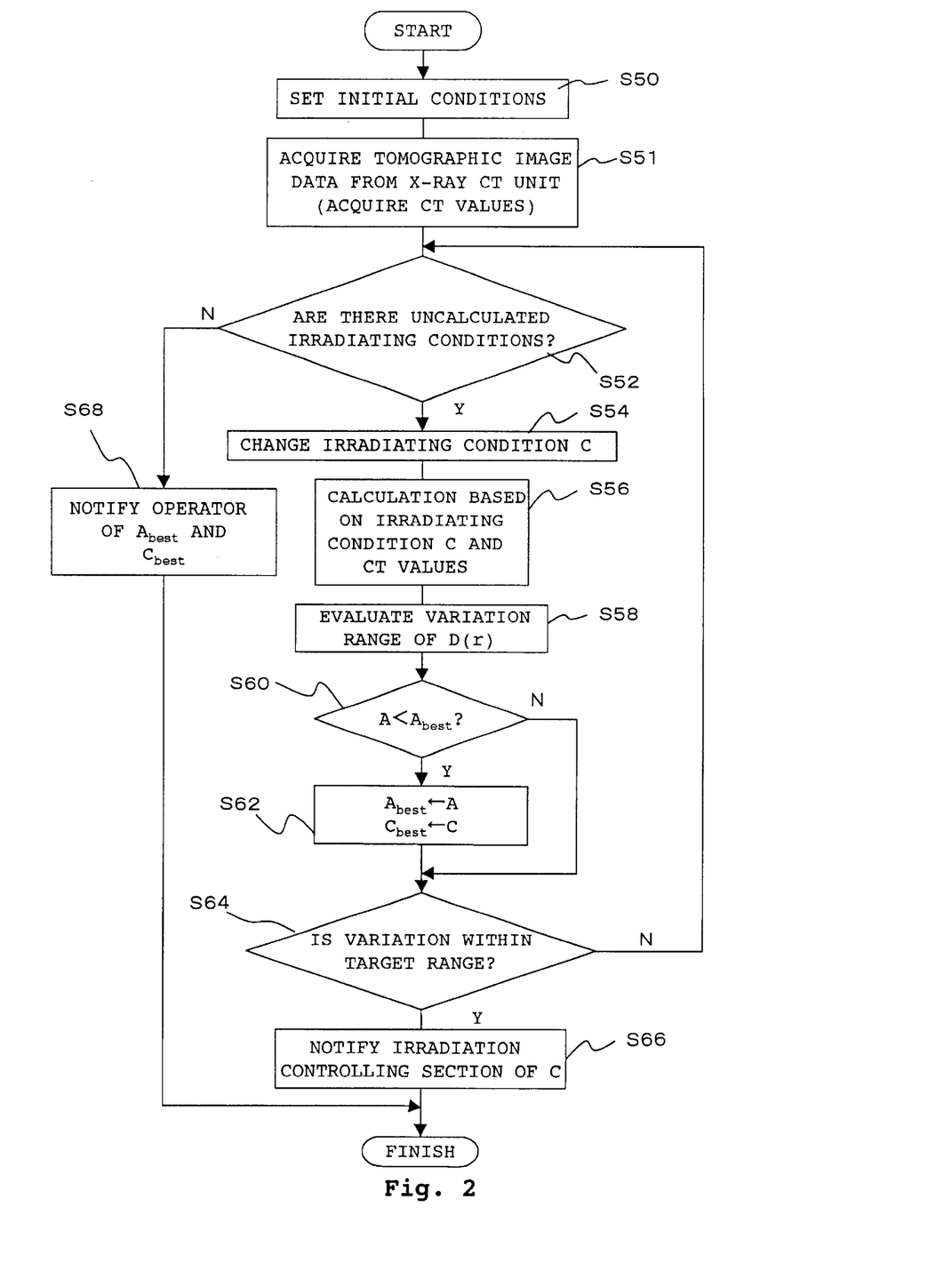
FIG. 2 is a flowchart showing the process carried out in an irradiating condition determining section.

FIG. 2 is a flowchart which briefly describes the process steps carried out in the irradiating condition determining section 8. As mentioned above, the tomographic image data captured by the X-ray CT unit 6 is transferred to the irradiating condition determining section 8. Upon starting the process for one object to be exposed 2, the irradiating condition determining section 8 sets initial conditions (S50) and acquires the tomo-graphic image data from the x-ray CT unit 6 (S51). After that, steps S52–S64 are repeated by changing irradiating conditions until a solution to an irradiating condition C under which an appropriate absorbed dose distribution D(r) is given is found, or no solution result is obtained otherwise.

The dose distribution has yet to be calculated for any irradiating condition C at the beginning of the procedure (S52). Therefore, the process proceeds to the irradiating condition changing step S54 where the initial values of the condition C are set instead of changing them. Herein, the irradiating condition C consists of a combination of the above-mentioned three parameters, i.e., energy E, irradiating direction θ, and irradiation dose R for each irradiating head.

After that, the irradiating condition determining section 8 runs a simulation calculation based on the irradiating conditions C set above and the CT values representing the density distribution data of the object to be exposed 2 acquired as tomographic image data, and determines a three dimensional distribution D(r) where r represents three dimensional coordinates, of the absorbed dose in the object to be exposed 2 (S56). Many computing methods are known for simulating the dose distribution for X-rays and electronic beams, respectively, ranging from adopting empirical data to faithfully calculating all physical events. Of these methods, a suitable method can be selected based on the allowable cost for computation, the required calculation accuracy, or the precision of controlling the radioactive ray irradiation. Since the present apparatus uses multiple irradiation heads to attain irradiation from different directions, the absorbed dose distribution D(r) is a combination of respective absorbed doses originated with each head.

Once the absorbed dose distribution is determined for the irradiating condition C set above, it is evaluated whether the variation of the determined distribution falls within the required reference range (S58). For instance, the absorbed dose distribution in the object to be exposed 2 has to be within a target range defined by predetermined upper and lower limits. In general, if the object to be exposed 2 is food or plant, the upper limit is determined so as to suppress the damage to the object below an allowable level, and the lower limit is determined to sufficiently accomplish the purpose of the irradiation such as sterilization. Thus, the upper limit depends generally on resistance to radioactive rays of the object to be exposed 2, while the lower limit depends on resistance to radioactive rays of bacteria or pests.

The irradiating condition determining section 8 calculates an evaluation value A at the step S58 to facilitate the comparison with other irradiating conditions. In this embodiment, the evaluation value A is used for notifying the operator that a particular irradiating condition C is selected, although it is not a solution but is considered optimal, when the solution having the variation of the absorbed dose distribution D(r) within the target range for any irradiating condition C could not be found.

The evaluation value A is calculated by, for example, integrating the second power of a difference between the actual absorbed dose distribution D(r) obtained in the step S56 and the intermediate value of the target distribution range with respect to a space V (or the coordinates r included in V) within the object to be exposed 2. Generally, as the evaluation value A becomes smaller, the distribution D(r) is more likely to fall within the target range and becomes more uniform.

It is also preferable to adopt an evaluation method using a deviation of the distribution D(r) from the target range. In this method the evaluation value A is calculated by integrating an absolute value of the deviation, or the second power thereof, with respect to the deviation space. Again, the distribution D(r) is more likely to fall within the target range as the evaluation value A is smaller, so the evaluation value can be used for judging the appropriateness of the distribution.

The irradiating condition determining section 8 stores the minimum value $A_{best}$ for the evaluation value A and an irradiating condition $C_{best}$ under which this minimum evaluation value is given. If the evaluation value A for the current irradiating condition C is smaller than $A_{best}$ (S60), both $C_{best}$ and $A_{best}$ are updated with the current irradiating condition C and the corresponding evaluation value A, respectively (S62). Subsequent to the step S62, whether the distribution D(r) was within the target range at the step S58 is judged by the step S64 and, if it is affirmative, the current irradiating condition C is output to the irradiation controlling section 16 (S66). Then, the process of determining the irradiating condition is finished.

If the current evaluation value A is more than or equal to the minimum value $A_{best}$ at the step S60, the process jumps to the judgement step S64 without updating the evaluation value or the like at the step S62. Even if the evaluation value A is not equal to the minimum value, the corresponding irradiating condition C can be a solution as long as the distribution D(r) is within the target range. Thus, the condition C is also output to the irradiation controlling section 16 (S66) and the process is finished. It should be noted that the reason for carrying out the solution judgement step S64 even if the evaluation value A is determined to be minimum by the step S60 is that the fact that the evaluation value is minimum is sometimes not equal to the fact that the solution is found depending on the definition of the evaluation value A. This corresponds to, for example, the former definition of the two definitions of the evaluation value A mentioned above. On the contrary, if the evaluation value A is defined differently, it is not considered that the solution is found when the evaluation value is not minimum. In this case, the process jumps to the step S52 from S60. This corresponds to, for example, the latter definition of the two definitions of the evaluation value A mentioned above.

Then, if it is detected by the judgement step S64 that the variation of the distribution D(r) is deviated from the target range, the corresponding irradiating condition C is considered unqualified as a solution, and the process goes to the next candidate irradiating condition C (S52).

If the judgement step S52 determines that calculations are done for all possible irradiating conditions C, it is indicated that no irradiating condition C that can be considered as a solution is found. In this case, the operator is notified that no solution was found, and the irradiating condition $C_{best}$ which gives the possible smallest evaluation value within the searched irradiation range is also notified together with the actual smallest value $A_{best}$ (S68) for his/her reference. Then, the irradiating condition determining process of the object to be exposed 2 is finished.

In the above process, once a certain irradiating condition C passes the solution judgement step S64, the process is ended in order to reduce the computational cost. It is also possible, however, to constitute the process so that after evaluating variations of the distribution with respect to all possible irradiating conditions C (S58), all conditions C which satisfy the solution judgement step S64 are extracted and the most suitable condition is selected as a solution. Here, the absorbed dose distribution D(r) having the minimum variation, i.e., having more uniform distribution, may be selected, for example.

The energy E of the irradiating condition C is changed, for example, every 1 MeV from 1 to 10 MeV for electronic beams and from 1 to 5 MeV for X-rays. The irradiation dose can also be changed stepwise within an appropriate range. When changing the irradiating condition C at the step S54, the possible combinations of parameter values can be set in predetermined order one by one. However, if feedback on the evaluation result of the distribution D(r) at the step S58 is given, it is possible to shorten the time taken to determine a solution. For instance, if the distribution D(r) is within the target range for an upper part of the object to be exposed 2, but is below the target range a lower part of the object 2, then it is possible to set the irradiating condition C having an increased energy E or irradiation dose R for the radioactive ray irradiating head arranged under the object.

As mentioned above, the target range largely depends on the types of objects to be exposed 2 and bacteria or pests to be terminated. In the process of quarantine, however, it is often required that the variation range should be restricted within about 10% of the absorbed dose.

Figure 3:
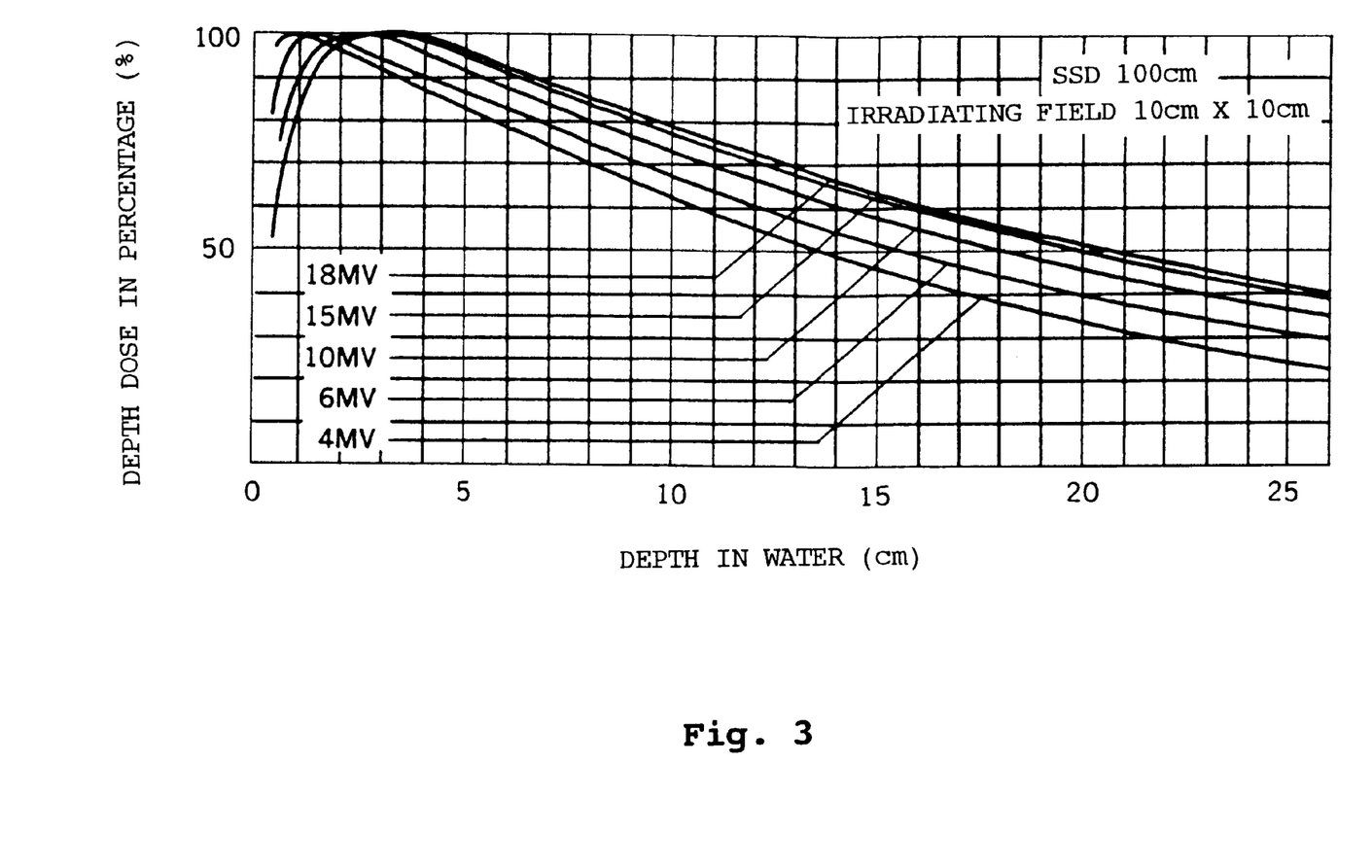
FIG. 3 is a graph showing depth dose curves of X-rays indicated in percentage.
Figure 4:
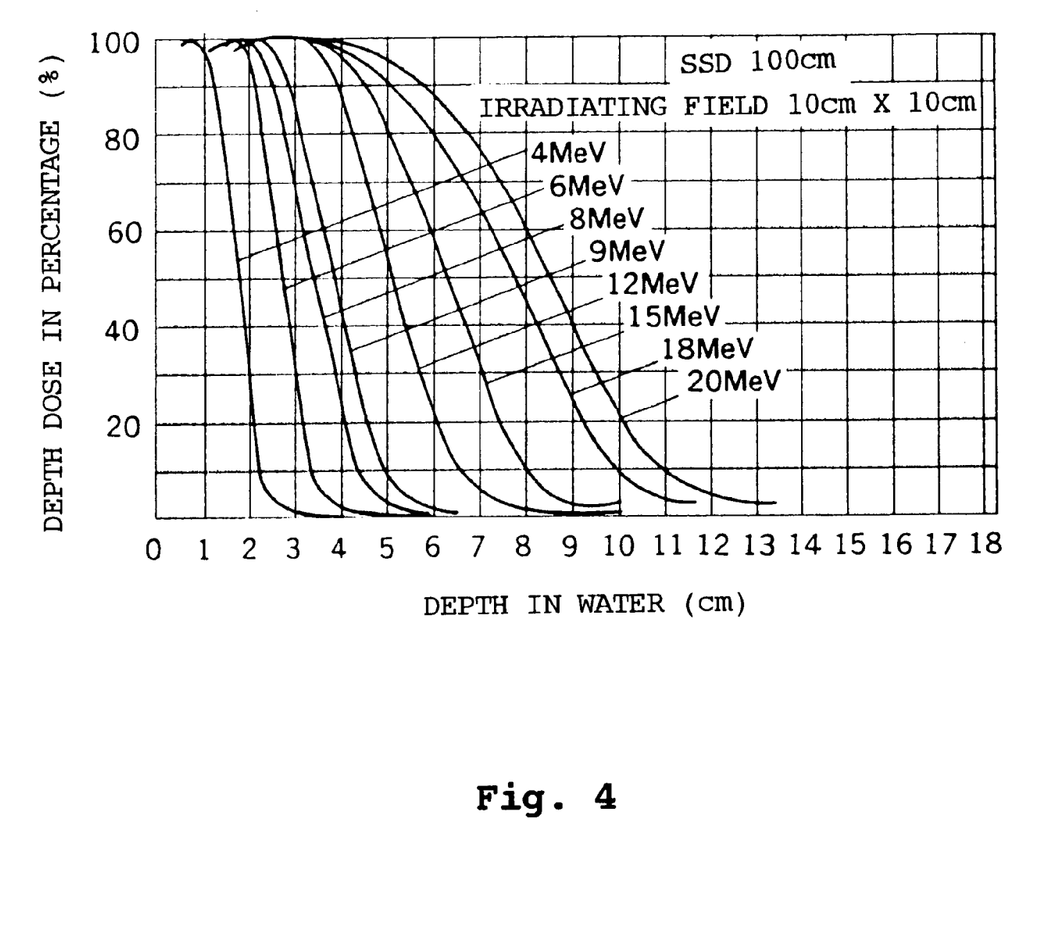
FIG. 4 is a graph showing depth dose of curves of electronic beams indicated in percentage.

FIGS. 3 and 4 are graphs showing a plurality of depth dose curves of X-rays and electronic beams, respectively, indicated in percentage in which each curve has a different energy parameter. As shown in the graphs, the penetrating distance in water is plotted along the horizontal axis and the relative absorbed dose for each energy level is plotted along the vertical axis with the maximum absorbed dose being 100%.

Positions of the contents of the box-like object to be exposed 2 plotted on the horizontal axes of FIGS. 3 and 4 depend on the thickness and materials of walls of the box. However, the variation can be kept within 10% for the distance range of about 2–3 cm in water for the X-rays having the energy of E=4MV, for example. If the contents of the object to be exposed 2 are packed relatively sparsely, such as cut flowers, the variation can be within 10% for a substantially wider depth range. The present apparatus recognizes the packing condition of the contents from the tomographic image data captured by the X-ray CT, and calculates the irradiating condition so that the variation is limited to, for example, 10% or less prior to irradiation. If it is desired to secure the uniformity for a wider depth range, it has been found qualitatively that the irradiation may be carried out from opposite directions so as to complementary overlap both distribution of absorbed doses. Again, the present apparatus can determine an appropriate irradiating condition by considering the density distribution of the object to be exposed 2.

Although the above process has been described to determine the individual irradiating conditions separately by capturing the tomographic image for each object to be exposed 2, it is also possible to use only one irradiating condition if a series of objects 2 of the same kind are provided, for example. In this case, the tomographic image is captured by the X-ray CT unit 6 for a certain object to be exposed 2 and the irradiating condition determining section 8 determines the irradiating condition, so that the steps of capturing the tomographic image and determining the irradiating condition are omitted for subsequent objects to be exposed 2 which can be considered to be irradiated under the same irradiating condition.

Also, it is assumed herein that the irradiation dose R from each radioactive ray irradiating head is determined such that the radiation strength on the horizontal surface of the object to be exposed 2 can be uniform. Instead, the irradiation dose R may be changed as the belt conveyor 10 moves. This can be realized by adjusting the moving speed of the belt conveyor 10 to change the irradiation time t. By changing the irradiation dose R along the moving direction of the object to be exposed 2, more freedom of searching the irradiating condition can be given, which facilitates the provision of a more suitable irradiating condition.

Also, the tomographic image capturing means formed by the X-ray CT apparatus is used in the above embodiment, but other nondestructive tomographic image capturing means can be used, such as a magnetic resonance imaging (MRI) apparatus which has been used in the medical field for many applications.

The above-described arrangement has a high processing ability due to the multiple radioactive ray irradiating heads which enable the simultaneous irradiation from different directions. Such irradiation from multiple directions can also be carried out using only one irradiating head. Specifically, such an arrangement is realized by providing one irradiating head in a rotating manner around the belt conveyor 10, as is often seen in many instances of the current radiotherapy. In this case, the head is made to rotate so as to irradiate the object to be exposed 2 sequentially from different directions while the object is stopped at a radioactive ray irradiating position. Although this arrangement is incomparable to the above arrangement having independent multiple accelerators in terms of processing ability, it may be advantageous in terms of downsizing and cost saving of the radioactive ray irradiating unit 14 because only one accelerator is used.

[Embodiment 2]

Figure 5:
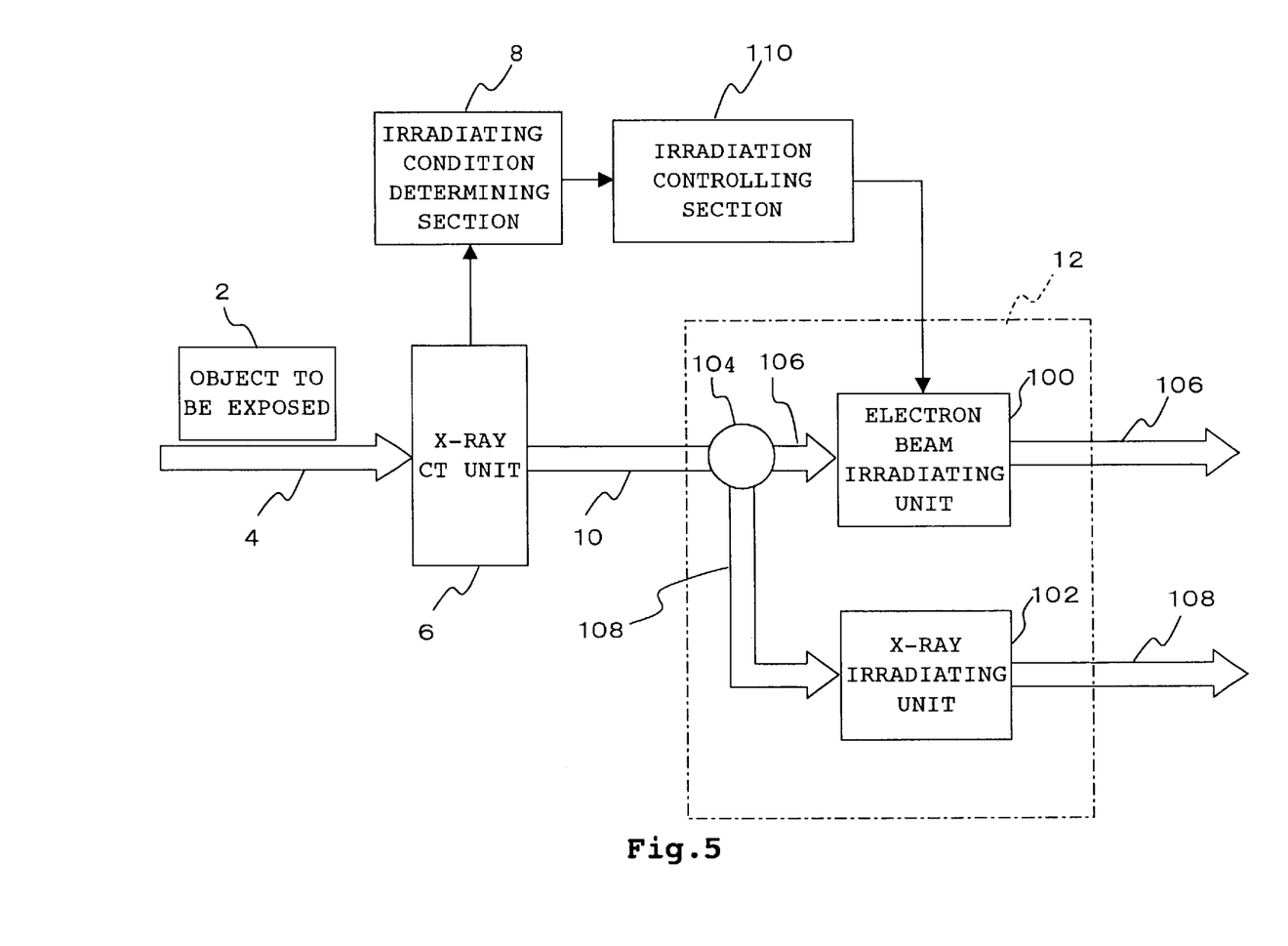
FIG. 5 is a schematic block diagram of a radioactive ray irradiating apparatus for plant quarantine according to a second embodiment of the present invention.

FIG. 5 is a block diagram showing a radioactive ray irradiating apparatus for plant quarantine according to a second embodiment of the present invention, in which the same reference numerals are given to the elements corresponding to those in the above embodiment and their description will not be repeated below. This apparatus differs from the apparatus of the former embodiment mainly in that a plurality of radioactive ray irradiating units are provided and each unit emits different types of radioactive rays. Specifically, the present apparatus includes an electronic beam irradiating unit 100 which is capable of irradiating electronic beams and an X-ray irradiating unit 102 which is capable of irradiating X-rays, both units being accommodated in the shield room 12.

The electronic beam irradiating unit 100 and the X-ray irradiating unit 102 may be arranged in series so that the objects to be exposed 2 can pass through the units sequentially by the belt conveyor, but the parallel arrangement as shown in the figure will be described below.

After the object to be exposed 2 enters the shield room 12 by the belt conveyor 10 from the X-ray CT unit 6, a dividing means 104 arranged at the end of the belt conveyor 10 divides the objects 2 so that they are put on either a belt conveyor 106 or 108 extending through the electronic beam irradiating unit 100 or the X-ray irradiating unit 102. The dividing means 104 may be a turntable, for example, which is controlled by an irradiation controlling section 110.

Corresponding to the ability of irradiating two types of radioactive rays, i.e., electronic beams and X-rays, the irradiating condition determining section 8 of the present apparatus considers the type of radioactive ray P as another parameter of the irradiating condition C. In other words, the irradiating condition C consists of three parameters, i.e., the energy E, the irradiating direction θ, and the irradiation dose R for the electronic beam irradiating unit 100 and the X-ray irradiating unit 102, respectively, plus an additional parameter as to the irradiating unit to be selected.

The irradiating condition determining process in the irradiating condition determining section 8 of the present apparatus is carried out in basically the same manner as in the process described earlier, except that the type of radioactive ray P is taken into consideration.

As shown in FIGS. 3 and 4, the depth dose curves indicated in percentage are largely different between X-rays and electronic beams, because of a large difference between the penetrating ability of the X-rays and the electronic beams, as is well known in the art. Due to this characteristic of radioactive rays, the X-rays are considered suitable for the irradiation of the object to be exposed 2 requiring the penetrating ability, while the electronic beams can be used for the irradiation of the object 2 when the penetrating ability is not such an important requirement. In general, the magnitude of required penetrating ability tends to be proportional to the size of the box (i.e., the dimensions of the box along the irradiating direction), but is not the only factor necessary for the accurate determination of the penetrating ability. With the present apparatus, the required penetrating ability can be determined accurately from the tomographic image data captured by the X-ray CT unit 6.

It should also be noted that the accelerators used in the radioactive ray irradiating unit can only accelerate charged particles. That is, the X-ray irradiating unit 102 uses the same accelerators as used in the electronic beam irradiating unit 100 to accelerate electrons, and projects the accelerated electrons to the target to generate X-rays by bremsstrahlung (braking radiation) of electrons. This means that the energy of X-rays cannot be greater than the energy of the original electrons. For instance, the energy conversion efficiency of the X-rays generated with the electrons having the energy of 5 MeV is about 7%. Thus, when a solution to the irradiating condition is found for both electron beams and X-rays, the energy efficiency is better using electron beams for irradiation.

If the required penetrating ability known from the tomographic image data is less than or equal to a predetermined value, the irradiating condition determining section 8 primarily searches for the irradiating condition C for using electron beams due to its superior energy efficiency and, if no such irradiating condition C is found, then proceeds to search for another irradiating condition C for using X-rays. In contrast, if the required penetrating ability is greater than the predetermined value, a solution is searched from the beginning only for the range of irradiating conditions C which use X-rays. Thus, a solution with better energy efficiency can be found effectively.

For instance, if the object to be exposed 2 includes strawberries, the object must be in the shape of a flat box as the packed strawberries cannot be stacked high in the box. To irradiate the top surface of the box vertically, it is likely that the solution to the irradiating condition for using electron beams is obtained. If the the object to be exposed 2 comprises grapefruits or the like that contain a relatively large amount of water and can be stacked in multiple layers in the box, the solution may indicate to use X-rays having a high penetrating ability.

Biological effectiveness of radioactive ray is different depending on the types of rays, even if the absorbed doses are the same. A concept of equivalent weight of dose is known as an index indicating the biological effectiveness or the like. However, since a quality factor applied for correcting the difference of biological effectiveness between X-rays and electron beams is approximately 1, the biological effectiveness can be regarded as approximately the same for both X-rays and electron beams when their absorbed doses are the same. In this embodiment, the irradiating condition determining section 8 determines the irradiating condition using the absorbed dose instead of the dose equivalent.

As described above, the radioactive ray irradiating apparatus according to the present invention projects radioactive rays based on the irradiating condition determined in advance by calculation by using the density distribution of the object to be exposed obtained from the tomographic image capturing means in such a manner that the variation of the absorbed dose distribution inside the object to be exposed is limited. This facilitates the realization of the uniform radioactive ray irradiation that enables the termination of bacteria or pests attached to the object to be exposed, such as plants or food products, with respect to all objects to be exposed, while preventing damages to the objects. As a result, the steps necessary for determining the irradiating condition can be minimized and the objects to be exposed can be treated with radioactive rays in a proper and reliable manner. In this way, safety of the objects such as foods is ensured.

With the radioactive ray irradiating apparatus according to the present invention, it is easy to find a more suitable irradiating condition, because the apparatus can emit different types of radioactive rays, i.e., electronic beams and X-rays having different curves indicating absorbed doses in substance.

Further, the radioactive ray irradiating apparatus according to the present invention includes the transportation means for moving the objects to be exposed so that the objects pass through the radioactive ray irradiating means, whereby the irradiation dose is adjusted easily in accordance with the moving speed of the transportation means.

While there has been described what are at present considered to be preferred embodiments of the invention, it will be understood that various modifications may be made thereto, and it is intended that the appended claims cover all such modifications as fall within the true spirit and scope of the invention.

What is claimed is:

1. A radioactive ray irradiating apparatus for projecting radioactive rays for sterilization, pasteurization, termination of pests, or inhibition of germination, comprising:

tomographic image capturing means for capturing a sectional image in a direction of projecting radioactive rays to obtain a density distribution of an object to be exposed; and     irradiating condition determining means for determining an irradiating condition based on said density distribution so that a variation of a dose distribution of projected radioactive rays within said object to be exposed falls within a predetermined reference range,     wherein radioactive ray irradiating means is controlled to project radioactive rays in accordance with said irradiating condition.

2. The radioactive ray irradiating apparatus according to claim 1, wherein types of radioactive rays which can be projected from said radioactive ray irradiating means are electron beams and X-rays, and     said irradiating condition determining means determines said irradiating condition including said types of radioactive rays.

3. The radioactive ray irradiating apparatus according to claim 2, further comprising transportation means for moving said object to be exposed from said tomographic image capturing means to said radioactive ray irradiating means in such a manner that said object to be exposed passes through said radioactive ray irradiating means at a speed corresponding to a necessary irradiation dose and a radioactive ray intensity of said radioactive ray irradiating means.

4. The radioactive ray irradiating apparatus according to claim 1, further comprising transportation means for moving said object to be exposed from said tomographic image capturing means to said radioactive ray irradiating means in such a manner that said object to be exposed passes through said radioactive ray irradiating means at a speed corresponding to a necessary irradiation dose and a radioactive ray intensity of said radioactive ray irradiating means.

5. The radioactive ray irradiating apparatus according to claim 1, wherein said tomographic image capturing means is an X-ray CT apparatus.

6. The radioactive ray irradiating apparatus according to claim 1, wherein said tomographic image capturing means is a magnetic resonance imaging (MRI) apparatus.

7. The radioactive ray irradiating apparatus according to claim 1, wherein said radioactive ray irradiating means has a plurality of irradiating heads which project radioactive rays from different directions.

8. The radioactive ray irradiating apparatus according to claim 1, wherein said irradiating condition determining means determines the irradiating condition including an energy of radioactive rays, an irradiating direction, and an irradiation dose.

9. The radioactive ray irradiating apparatus according to claim 1, wherein said irradiating condition determining means defines an upper limit of said dose distribution of the projected radioactive rays based on an allowable limit of damages to said object to be exposed, and also defines a lower limit of said dose distribution so as to accomplish the purpose of projecting radioactive rays, that is, sterilization, pasteurization, termination of pest, or inhibition of germination.

10. The radioactive ray irradiating apparatus according to claim 1, wherein said transportation means is a belt conveyor.

11. The radioactive ray irradiating apparatus according to claim 1, wherein said radioactive ray irradiating means can variably adjust the irradiation dose.

12. The radioactive ray irradiating apparatus according to claim 1, wherein the projected dose can be changed by adjusting the transportation speed of said transportation means.

* * * * *